United States Patent
Groemping et al.

(10) Patent No.: US 10,301,251 B2
(45) Date of Patent: May 28, 2019

(54) EXTRACTIVE WORKUP OF A SODIUM-SALT-CONTAINING MMA-METHANOL MIXTURE

(71) Applicant: Evonik Roehm GmbH, Darmstadt (DE)

(72) Inventors: Matthias Groemping, Darmstadt (DE); Steffen Krill, Muehltal (DE); Alexander Lygin, Griesheim (DE); Milica Lukic, Frankfurt (DE); Steffen Finger, Mainz-Kastel (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 15/760,030

(22) PCT Filed: Sep. 14, 2016

(86) PCT No.: PCT/EP2016/071608
§ 371 (c)(1),
(2) Date: Mar. 14, 2018

(87) PCT Pub. No.: WO2017/046110
PCT Pub. Date: Mar. 23, 2017

(65) Prior Publication Data
US 2018/0251419 A1    Sep. 6, 2018

(30) Foreign Application Priority Data

Sep. 16, 2015 (EP) .................... 15185434

(51) Int. Cl.
| | | |
|---|---|---|
| *C07C 67/39* | (2006.01) | |
| *C07C 67/54* | (2006.01) | |
| *C07C 67/58* | (2006.01) | |
| *C07C 45/28* | (2006.01) | |
| *C07C 45/29* | (2006.01) | |
| *C07C 45/67* | (2006.01) | |

(52) U.S. Cl.
CPC .............. *C07C 67/39* (2013.01); *C07C 45/28* (2013.01); *C07C 45/29* (2013.01); *C07C 45/673* (2013.01); *C07C 67/54* (2013.01); *C07C 67/58* (2013.01); *Y02P 20/582* (2015.11)

(58) Field of Classification Search
None
See application file for complete search history.

(56) References Cited

U.S. PATENT DOCUMENTS

| | | |
|---|---|---|
| 5,969,178 A | 10/1999 | Okamoto et al. |
| 7,012,039 B2 | 3/2006 | Watanabe et al. |
| 9,890,105 B2 | 2/2018 | Krill et al. |

FOREIGN PATENT DOCUMENTS

WO    2014/170223 A1    10/2014

OTHER PUBLICATIONS

International Search Report dated Nov. 11, 2016, in PCT/EP2016/071608, filed Sep. 14, 2016.

*Primary Examiner* — Ana Z Muresan
(74) *Attorney, Agent, or Firm* — Oblon, McClelland, Maier & Neustadt, L.L.P.

(57) ABSTRACT

The present invention relates to a process for preparing methyl methacrylate by direct oxidative esterification of methacrolein. Methyl methacrylate is used in large amounts for preparing polymers and copolymers with other polymerizable compounds. In addition, methyl methacrylate is an important synthesis unit for a variety of specialty esters based on methacrylic acid (MAA) which can be prepared by transesterification with the appropriate alcohol. There is consequently a great interest in very simple, economic and environmentally friendly processes for preparing this starting material.

In particular the present invention relates to an optimized workup of the reactor effluent from the oxidative esterification of methacrolein by means of which process waste streams can be minimized and process water can be recycled in optimal fashion. The methacrylic acid generated in the process is also optimally recovered and isolated or converted into the commodity alkyl methacrylate. This process moreover has the advantage that fewer demands than described in the prior art are placed on plant apparatus configuration.

13 Claims, 1 Drawing Sheet

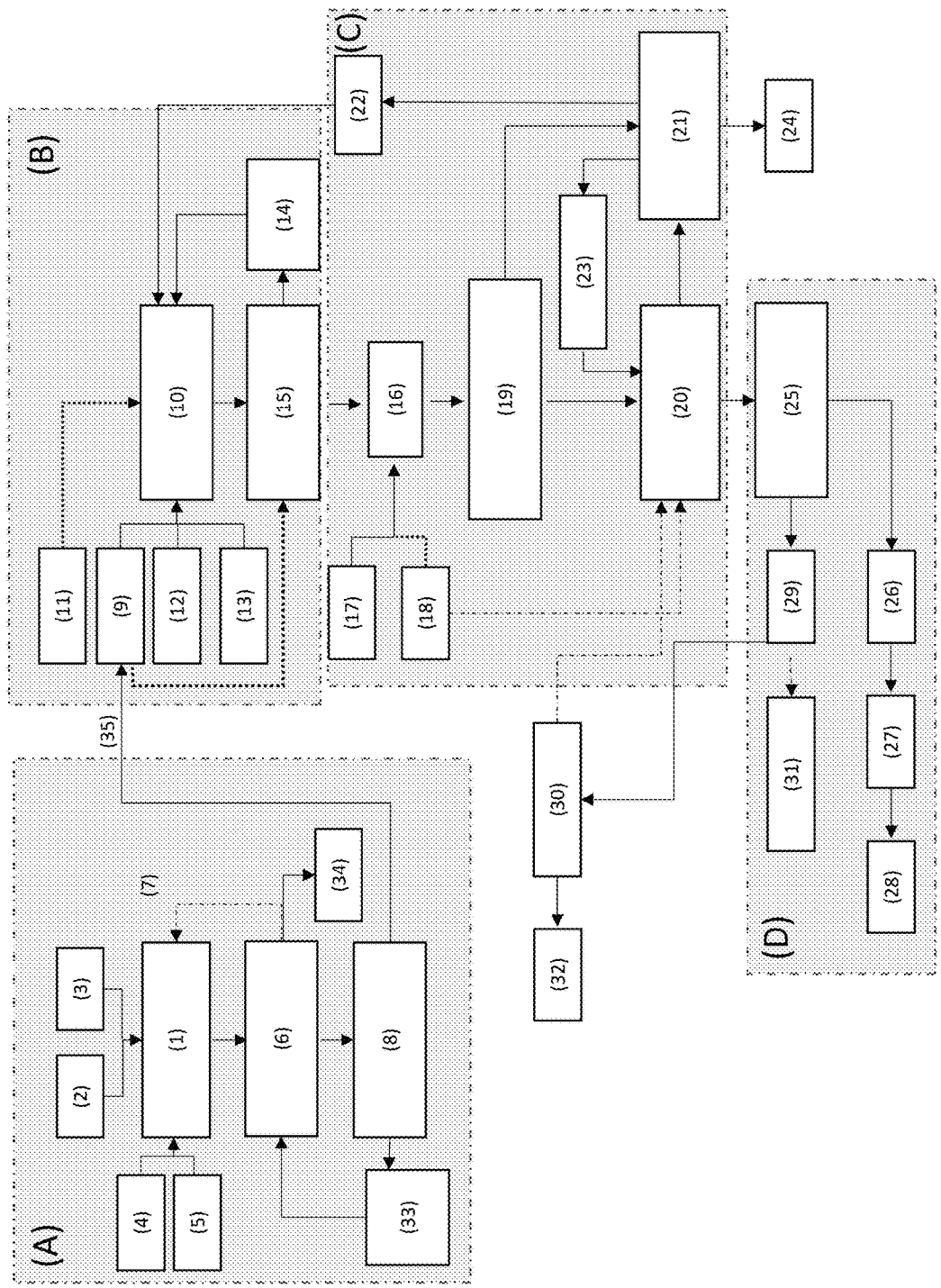

EXTRACTIVE WORKUP OF A SODIUM-SALT-CONTAINING MMA-METHANOL MIXTURE

FIELD OF THE INVENTION

The present invention relates to a process for preparing methyl methacrylate by direct oxidative esterification of methacrolein. Methyl methacrylate is used in large amounts for preparing polymers and copolymers with other polymerizable compounds. In addition, methyl methacrylate is an important synthesis unit for a variety of specialty esters based on methacrylic acid (MAA) which can be prepared by transesterification with the appropriate alcohol. There is consequently a great interest in very simple, economic and environmentally friendly processes for preparing this starting material.

In particular the present invention relates to an optimized workup of the reactor effluent from the oxidative esterification of methacrolein by means of which process waste streams can be minimized and process water can be recycled in optimal fashion. The methacrylic acid generated in the process is also optimally recovered and isolated or converted into the commodity alkyl methacrylate. This process moreover has the advantage that fewer demands than described in the prior art are placed on plant apparatus configuration.

PRIOR ART

Methyl methacrylate (MMA) is currently produced by a variety of processes proceeding from $C_2$, $C_3$ or $C_4$ synthesis units. In one of the processes MMA is obtained by gas-phase oxidation of isobutylene or tert-butanol with atmospheric oxygen over a heterogeneous catalyst to afford methacrolein and subsequent oxidative esterification of methacrolein using methanol. This process, developed by ASAHI, is described, inter alia, in publications U.S. Pat. Nos. 5,969,178 and 7,012,039. A particular disadvantage of this process is the very high energy requirement. In a development of the process the methacrolein is obtained from propanal and formaldehyde in the first stage. Such a process is described in WO 2014/170223.

U.S. Pat. No. 5,969,178 describes such a process for oxidative conversion of isobutene or tert-butanol into methacrolein and subsequent oxidative esterification to MMA. In this second stage a liquid mixture of methacrolein and methanol with reduced water content is reacted with molecular oxygen and a palladium catalyst, wherein said catalyst is usually in supported form as a palladium-lead catalyst.

In a first distillation stage a mixture of methacrolein and methanol is then removed from the crude product of the oxidative esterification below the top of the column while low-boiling constituents are removed overhead. The MMA-containing bottoms product is then passed into a second distillation stage in which an azeotrope of methanol and saturated hydrocarbons is removed overhead. The bottoms product comprising the crude MMA is sent to a further workup while methanol is isolated from the overhead fraction by means of a phase separator and a third distillation column and passed back into the reactor. It is to be borne in mind that the methanol can contain relatively large amounts of water on account of the azeotrope formed and must therefore be sent to a dewatering. As an alternative to this process U.S. Pat. No. 5,969,178 discloses a workup in only one column wherein in said column it is imperative that the feed be situated above the column bottom. Low-boiling constituents from the reactor effluent are removed from this column overhead. Remaining in the column bottom is a mixture of crude MMA and water which is to be sent to a further workup. Via a sidestream whose exact position must first be determined, said position being adjustable by addition of various sieve trays, a mixture of methacrolein and methanol intended for return to the reactor is finally taken off from the column. U.S. Pat. No. 5,969,178 itself indicates that such a process is difficult to perform on account of a variety of azeotropes. Particularly methacrylic acid, which is always present as a byproduct, moreover plays an important role. According to this process, despite the silence of U.S. Pat. No. 5,969,178 on this issue, the methacrylic acid would be removed in a manner such that it remains in a phase to be sent for disposal and an isolation would be of only limited attractiveness. However, this results in a fall in the overall yield of methacrylic products of this process.

U.S. Pat. No. 7,012,039 discloses a workup of the reactor effluent from the oxidative esterification which is somewhat of a departure. Here, in a first distillation stage over screen trays methacrolein is distilled off overhead and the aqueous MMA-comprising mixture from the column bottom is passed into a phase separator. In said phase separator the mixture is pH-adjusted to a pH of about 2 by addition of sulfuric acid. The separation of the sulphuric-acid-acidified water from the organic/oil phase is then effected by means of centrifuging. This oil phase is separated in a further distillation into high-boiling constituents and an MMA-containing phase withdrawn overhead. The MMA-containing phase is then separated from low-boiling constituents in a third distillation. This is even followed by a fourth distillation for final purification.

The problem with this process is the sulfuric acid which needs to be added in large amounts and can have corrosive effects on parts of the plant. Accordingly these parts, such as in particular the phase separator or else the second distillation column, must be fabricated from suitable materials. Moreover, U.S. Pat. No. 7,012,039 is silent regarding the handling of the simultaneously generated methacrylic acid or the residual methanol remaining in the product. However it can be assumed that the former is coremoved in the distillation stages while the methanol can be obtained and returned with the methacrolein only partially while the remainder is probably lost in the third distillation stage.

WO 2014/170223 describes a similar process to U.S. Pat. No. 7,012,039. The only difference is that in the actual reaction the pH is adjusted in a circuit by addition of a methanolic sodium hydroxide solution. This serves, inter alia, to protect the catalyst. Moreover, the removal of the aqueous phase in the phase separation is simpler on account of the salt content. However, another consequence is that the methacrylic acid formed is in the form of sodium salt and is later removed and disposed of with the aqueous phase. Admittedly, in the variant where sulfuric acid is added in the phase separation the free acid is recovered. However, instead, sodium (hydrogen) sulfate is generated which can lead to other problems upon disposal.

In summary, the following aspects of the prior art processes, especially in combination with one another, are in need of improvement:
highest possible yield
obtainment of the byproducts generated in the form of methacrylic acid and isolation thereof or return to the oxidative esterification
highest possible extent of recycling of the unconverted methanol reducing the amounts of sulfuric acid and water to be added cleanest possible disposal streams/offgases

PROBLEM

The problem addressed by the present invention in view of the prior art is therefore that of providing a technically improved process for oxidative esterification of methacrolein that is not afflicted with the disadvantages of conventional processes.

A particular problem addressed by the present invention was that of providing an improvement in the workup of the crude product from an oxidative esterification of methacrolein and methanol to afford MMA and thus to improve the overall yield of such a process compared to the prior art.

A further problem addressed was that of recycling and converting in the process into the target products, to the greatest possible extent, the greatest possible number of unconverted reactants or byproducts or intermediates formed in the process, in particular methanol, methacrolein, methacrylic acid and water, and optionally isolating the methacrylic acid as such.

A further problem addressed was that of isolating/recycling methacrylic acid from the system using the smallest possible amounts of added acid. The local concentration and the overall consumption of this acid shall be kept as low as possible.

A further problem addressed by the present invention was that of designing the workup so as to ensure the smallest possible number of points of contact with strong and thus corrosive acids in the plant. A consequent problem addressed by the present invention was in turn that of ensuring that, in terms of the material of construction, the overall plant needs to be provided with an appropriate acid protection only to a limited extent.

A further particular problem addressed was that of providing a process that can be operated with the lowest possible disposal cost, in particular through reduced generation of organic constituents and acids in the waste stream.

The process shall furthermore be inexpensive, in particular in terms of the materials to be employed for construction of the plant, compared to the prior art.

SOLUTION

The embodiments of the present invention will be hereinafter explained by reference to the FIGURE.

The problems are solved by a process for producing MMA where in a first reaction stage (A) in a reactor I (1) methacrolein is produced and in a second reaction stage (B) in a reactor II (10) said methacrolein is oxidatively esterified with an alcohol, preferably with methanol, to afford an alkyl methacrylate, thus preferably to afford MMA, wherein the process comprises a novel workup (C) of the crude product discharged from the second reactor (10). In this workup (C) a low-boiling fraction comprising mainly alcohol is obtained from a mixture comprising water, the alcohol, at least one alkali metal salt, methacrylic acid and a strong acid in a distillation column IV. This alcohol is then reused for producing alkyl methacrylates.

In accordance with the invention a strong acid is to be understood as meaning an acid stronger than methacrylic acid. This means that the acid has a smaller PKA than methacrylic acid under standard conditions. A particularly preferred inorganic acid is in this case sulfuric acid. The less preferred organic acids may be, for example, methanesulfonic acid or toluenesulfonic acid. An example of a further suitable mineral acid is phosphoric acid.

Preferably in this workup (C) a stream comprising water, the alcohol, at least one alkali metal salt, an organic and/or inorganic, preferably inorganic, acid and methacrylic acid is separated in a distillation stage (21), referred to hereinbelow as distillation column IV (21), into a low-boiling fraction (22) comprising the alcohol, a sidestream fraction (23) comprising water and methacrylic acid and a bottoms fraction (24) comprising water, the organic and/or inorganic acid and the alkali metal salts thereof. What is novel here is in particular the separately taken-off sidestream (23).

The process for synthesizing MMA which comprises the two above-cited reaction stages (A) and (B) may be read up in particular in U.S. Pat. Nos. 5,969,178, 7,012,039 and WO 2014/170223. The first stage of the process for synthesizing the methacrolein is freely choosable according to the invention. The process according to the invention is applicable to a first stage synthesis based either on tert-butanol or isobutylene or on propanal and formaldehyde. It is preferable when the oxidative esterification is carried out in the liquid phase at a pressure of 2 to 100 bar, preferably at a pressure in the range from 2 to 50 bar, and a temperature in the range from 10° C. to 200° C. with a heterogeneous catalyst. The heterogeneous catalyst generally comprises supported gold-containing nanoparticles having a particle size less than 20 nm, preferably between 0.2 and 20 nm. The reaction stage (A) may comprise an optional and less preferred distillation column II for removal of low-boilers, such as remaining propionaldehyde, and/or of high boilers, such as dimeric methacrolein.

This distillation stage is preferably a distillation column IV (21) that is integrated into the following set up. The crude product from the oxidative esterification is initially freed of methacrolein and, partially, of the alcohol, such as, for example, methanol in a distillation column III (15). This affords a stream comprising an alkyl methacrylate, preferably MMA, water, an alkali metal methacrylate and/or methacrylic acid and methanol. This stream is then separated in an extraction (20) and/or in a phase separation (19) present without an extraction or arranged upstream of said extraction into a light phase comprising an alkyl methacrylate, preferably MMA, and methacrylic acid and a heavy phase comprising water, methanol and the alkali metal methacrylate. This heavy phase is then passed into the distillation column IV (21) and the sidestream from the distillation column IV (21) taken off there is returned to the extraction (20). In this process mode the addition of the strong acid (for example as (17)) is also effected here, for example upstream of the feed into the phase separation (19) or into the extraction (20).

It is preferable when the feeding of the strong acid (e.g. 17) is effected between the distillation column III (15) and the extraction (20), into the extraction (20) itself, into the heavy phase taken off from the extraction (20) and/or into the distillation column IV (21). It is particularly preferable when the stream from distillation column III comprising the alkyl methacrylate is admixed with the strong acid.

In the case where the feeding of the strong acid is already at least partially effected upstream of the extraction (20) the stream from distillation column III (15) also already comprises proportions of this acid and corresponding alkali metal salts of the acid. In this case the methacrylic acid is present as free acid.

A feature of the present invention that is essential according to the invention is the distillation column IV (21), particularly preferably comprising the sidestream takeoff.

This means in particular that aspects described hereinbelow and not specifically directed to the preferred embodiment having a distillation column III (15) and an extraction (20) are not limited to these embodiments. In addition, the distillation column IV (21) may also be referred to as a desorption column.

This preferred workup is moreover preferably characterized in that the feed into the extraction, the extraction itself, the heavy phase taken off from the extraction and/or the distillation column IV (21) is admixed with the strong, preferably exclusively inorganic, acid. It is particularly preferable when the feeding of the strong acid into the heavy phase from the extraction is effected directly upstream of the distillation column IV.

In a further optional advantageous variant of the invention the stream from distillation column III (15) comprising the alkyl methacrylate is passed into a phase separator (19) from which an organic phase is passed on into the extraction (20) and an aqueous phase is passed on into the distillation column IV (21).

In a further optional advantageous variant of the invention the stream from distillation column III (15) comprising the alkyl methacrylate is passed into a mixer (16) into which the strong acid and optionally water are sent and mixed with the alkyl-methacrylate-comprising stream and that this mixture is subsequently passed into the phase separator (19) or directly into the extraction (20). The admixing with the strong acid also brings about an acetal cleavage. The acetals may be present in the mixture as an impurity. Such an acetal cleavage is described, for example, in JP11-302224A.

A great advantage of this procedure is that in the distillation column IV (21) the alkali metal methacrylate is virtually completely converted into methacrylic acid in the presence of the strong and, in particular, inorganic acid and passed back into the extraction (20) via the sidestream (23). Said methacrylic acid is then discharged from the system at that point as a constituent of the low-boiling fraction together with the MMA and can be isolated. In this way this process affords an altogether higher yield of desired $C_4$ products. Otherwise the methacrylic acid, in particular in the form of an alkali metal salt, would be taken off from the distillation column IV (21) in the aqueous phase and sent, for example, for disposal (24).

It is particularly preferable to feed all or at least most of the inorganic acid into the heavy phase from the extraction directly upstream of the distillation column IV (21). This embodiment has the great advantage that only this feed, the column of the distillation column IV (21) and the conduit for takeoff of the bottoms fraction (24) from this column as well as the components downstream of said conduit need to be fabricated from a particularly corrosion-resistant material or with a corrosion-resistant coating. An example of such a corrosion-resistant material is zirconium. This embodiment is comparatively less demanding of the extraction (20) and the distillation column III (15) and a simpler material may be employed which in turn economizes on capital costs.

It is also preferable when the strong acid is added to the respective stream, in particular downstream of the distillation column III (15) or into the extraction (20), only in an amount sufficient to ensure that the pH in the extraction is always ≥3.

In addition to the described preferred setup other constructions comprising the inventive distillation column IV (21) with the preferably present sidestream takeoff are also conceivable in accordance with the invention. Thus, a plant where the distillation column III (15) is eschewed is conceivable. A simple phase separation, for example in the form of a centrifuge, would also be conceivable in place of the extraction. It is also possible to connect a plurality of distillation stages, phase separators and/or centrifuges in series for takeoff of the individual fractions.

It is nevertheless possible in a particular embodiment to feed small amounts of the strong acid into the respective stream downstream of the distillation column III (15) or in the extraction (20). It is then necessary, if the intention is still to use the same materials for the distillation column III (15) and the extraction (20), to choose the inorganic acid feed amount such that the relevant stream is adjusted to a pH of not less than 3. The advantage of this variant is that a portion of the alkali metal methacrylate is already converted into the free acid upstream of or at the feed of the crude MMA into the extraction (20) and can already be taken off from the system upstream of the conduit into the distillation column IV (21).

In particular, the cited alkali metal salt is sodium sulfate, the alkali metal methacrylate is sodium methacrylate and the inorganic acid is sulfuric acid. However it is also conceivable to employ other alkali metals, for example potassium. It is also very preferable for all of the cited stages, and thus the particular entire process, to be carried out continuously irrespective of the exact configuration.

Described below are processes for further processing of the streams taken off from the described workup:

The light phase which in the preferred embodiment is taken off from the extraction may, for example, be worked up over at least two, preferably at least three, further distillation stages. To this end the crude MMA initially has high-boiling constituents taken off from it in a distillation column V (25) and then has low-boiling constituents taken off from it in a distillation column VI (26). This may optionally be followed by a final purification in a distillation column VII (27), for example for renewed removal of further low-boiling constituents. The purified alkyl methacrylate, in particular MMA (28), is thus generated, for example, as a tops stream from a third distillation stage while the methacrylic acid can be isolated as bottoms from the first (29) and/or third distillation column and may optionally be sent to a further distillation stage. Alternatively one or more or all of these distillation stages may, in particular for purification of the methacrylic acid, be replaced by a crystallization. Independently of the procedure, a fraction composed predominantly of methacrylic acid (29) and a fraction composed predominantly of MMA (28) are obtained.

The fraction composed predominantly of methacrylic acid (29) may then be esterified with an alcohol to afford an alkyl methacrylate. In particular the methacrylic acid may be esterified with methanol to afford MMA. This is preferably effected in a separate reactor (30) and not by returning to the reactor II (10). The reason for this is that either an excessively high acid content in the reactor for oxidative esterification would damage the catalyst employed there or that—in particular—a pH of about 7 is established there by addition of an alkali metal hydroxide, for example sodium hydroxide, which would again convert the methacrylic acid into an alkali metal salt and thus impede an esterification.

By contrast, the low-boiling fractions from the distillation column III (15) comprising the methacrolein remaining in the crude product from the oxidative esterification and a fraction of the unconverted methanol may preferably be passed back into the reactor for oxidative esterification (10) in the second reaction stage. The same also applies for the low-boiling fraction (22) from the distillation column IV

(21) comprising predominately the remaining methanol. This too is preferably passed back into the reactor of the second reaction stage (10).

In particular, the low-boiling fraction from the distillation column IV comprises more than 60 wt %, preferably more than 65 wt %, of alcohol and less than 20 wt %, preferably less than 10 wt %, of water. The bottoms fraction comprises in particular more than 60 wt %, preferably more than 80 wt %, of water and the preferably present sidestream fraction from the distillation column IV comprises in particular more than 80 wt %, preferably more than 95 wt %, of water and less than 5 wt %, preferably less than 1 wt %, of alcohol.

The heavy phase also referred to as the bottoms fraction (24) from the second distillation column IV (21) may finally be sent for disposal (24), for example to a biological workup or an oxidative incineration.

It is particularly preferable when the sidestream (23) from the column of the distillation column IV (21) is withdrawn at a point in this column in which the alcohol content, and preferably the methanol content, is less than 1 wt %. The column preferably comprises sieve trays so that the sidestream (23) is taken off in liquid form and need not be additionally condensed. However, when taken off in liquid form the sidestream (23) could contain a fraction of the strong acid, in particular sulfuric acid, which would thus be passed back into the extraction (20). In the case where these amounts are only small and a pH above 3 is thus achieved in the extraction, this does not pose a major problem. However, should the sidestream (23) be taken off such that the acid content is greater, the extraction (20) would also have to be constructed from an appropriate corrosion-resistant material. Alternatively and particularly preferably the lower part of the distillation column IV (21) comprises a dividing wall. In this embodiment the column feed into the distillation column IV (21) is supplied at the upper end of the dividing wall and the side draw is positioned at a point on the other side of the dividing wall such that at said point the concentration of the strong acid is less than 0.1 wt % while the alcohol content is less than 1 wt %. In this case the sidestream may preferably be taken off in liquid form at the upper edge of this side of the dividing wall. This variant additionally has the great advantages that, in particular, the water on the takeoff side of the dividing wall hardly contains any sulfur compounds and that a longer residence time for the reaction of the alkyl methacrylate with the sulfuric acid is achieved on the other side of the dividing wall. It is then also possible to construct the conduit for transferring the sidestream back into the extraction (20) from less corrosion-resistant material. Distillation columns comprising a dividing wall may be read up, for example, in N. Asprion, G. Kaibel, Chem. Eng. and Process., 49 (2010), 139-146 or in I. Dejanovic et al., Chem. Eng. and Process., 49 (2010), 559-580.

It is particularly preferable to additionally install a heat exchanger into the plant by means of which the sidestream fraction (23) from the distillation column IV (21) is cooled before introduction into the extraction (20) and the heavy phase from the extraction (20) is simultaneously heated before introduction into the distillation column IV (21).

Irrespective of the specific embodiments of the process according to the invention said process has the great advantage compared to the known processes of the prior art, which varies only in the particular extent thereof, that in particular the local concentrations of the strong acid, such as in particular sulfuric acid, can be locally controlled and kept low in particular in the distillation stage III (15), the optional phase separator (19) and the extraction (20) as well as in the conduits and optional further component parts situated therebetween. This not only has the advantage that fewer corrosion-resistant materials can be employed but in particular also that the alkyl methacrylate, the therefor-employed and remaining raw materials and the byproducts formed are exposed to this acid to a lesser extent, if at all. This would result in the formation of further byproducts coupled with a reduced yield and an eventual discolouring of the end product. A simultaneous advantage is that altogether less acid needs to be employed.

A further very great advantage of the present invention is that the bottoms fraction (24) comprises less acid, product, reactants and byproducts. The recycling of the removed products alkyl methacrylate and methacrylic acid results in a marked enhancement of the $C_4$ yield of the overall process. The removal of the reactants, in particular of the alcohol, and the optional recycling into reactor II (10) further enhances the efficiency of the process. In particular, however, the aqueous bottoms fraction (24) is less contaminated with all of these cited constituents which firstly simplifies the disposal of this fraction and further also results in a reduced environmental burden even for proper disposal. In particular this bottoms stream (24) from the distillation column IV (21) may be sent to a further separating stage to recover water and methacrylic acid and to concentrate the salt-containing waste stream. Such a separating stage may be, for example, a stripping column, a membrane separating stage or a combination of various such elements. A stripping column here is run markedly hotter and thus faster than the distillation column IV (21). Such a further workup serves in particular to effect recovery and recycling of methacrylic acid and water from the then concentrated, salt-containing waste stream.

In a particularly preferred variant the bottoms stream is worked up such that the salt concentration is close to the concentration of a saturated solution after the concentrating operation. This advantageously also minimizes the amount of methacrylic acid in the waste stream. It is also possible to generate two waste streams via an appropriate arrangement of different membrane separation stages for example. One of these two streams is then highly concentrated in terms of salt and byproduct content while the other is composed predominantly of water. This has the advantage that the low-concentration second waste stream may be sent, for example, for biological disposal. The highly concentrated stream is generally sent to a thermal oxidizer.

LIST OF REFERENCE NUMERALS (A) synthesis and isolation of the methacrolein ((1)-(8), (33)-(35))
(1) reactor I for methacrolein synthesis
(2) formaldehyde feed
(3) propionaldehyde feed
(4) base I feed
(5) acid I feed
(6) distillation column I, catalyst removal
(7) optional return of catalyst fraction to reactor I
(8) MAL phase separation, methacrolein isolation
(33) return of MAL-containing, aqueous phase to distillation column I (6)
(34) waste stream from methacrolein synthesis
(35) stream for transferring methacrolein from MAL synthesis (A) into oxidative esterification (B); optionally but not preferably comprising a distillation column II (B) oxidative esterification of the methacrolein to afford an alkyl methacrylate and recycling of the methacrolein ((9)-(15))
(9) methacrolein stream feed into reactor II
(10) reactor II for oxidative esterification of the methacrolein
(11) alcohol feed (generally methanol feed)
(12) oxygen/air feed
(13) base II feed
(14) recycling stream comprising methacrolein and alcohol
(15) distillation column III for separating methacrolein and partially alcohol from crude alkyl methacrylate
(C) inventively preferred separation of the reactor effluent from reactor II ((16)-(24))
(16) optional mixer
(17) acid II feed
(18) optional water feed
(19) phase separation
(20) extraction
(21) inventive distillation stage (distillation column IV)
(22) low-boiling fraction comprising alcohol for return to reactor II
(23) sidestream fraction comprising water and methacrylic acid for return to the extraction stage (20), mixer (16) or phase separation (19).
(24) bottoms fraction comprising water, acid II and the alkali metal salts thereof for disposal or further workup
(D) preferred workup of the crude alkyl methacrylate (e.g. crude MMA) ((25)-(32))
(25) distillation column V for removal of high boilers
(26) distillation column VI for removal of low boilers
(27) distillation column VII for final purification of the alkyl methacrylate
(28) alkyl methacrylate product stream
(29) methacrylic-acid-containing stream from distillation column V (25)
(30) optional esterification of the methacrylic acid to afford alkyl methacrylate including separation of an alkyl-methacrylate-containing phase from a waste phase
(31) optional isolation of pure methacrylic acid as second product
(32) waste stream from the esterification (30)

The invention claimed is:

1. A process for producing methyl methacrylate, comprising:
producing methacrolein in a reactor I;
oxidatively esterifying the methacrolein with methanol to produce a reaction product comprising methyl methacrylate in a reactor II;
releasing methacrolein and, partially, methanol from the reaction product comprising methyl methacrylate in a distillation column III, to obtain a stream comprising methyl methacrylate, water, an alkali metal methacrylate and/or methacrylic acid and methanol;
mixing the stream with a strong acid;
separating the stream comprising the strong acid in a phase separation and/or an extraction into a light phase comprising methyl methacrylate and methacrylic acid and a heavy phase comprising water, methanol, at least one alkali metal salt, methacrylic acid, and the strong acid;
passing the heavy phase directly or indirectly into a distillation column IV,
obtaining a low-boiling fraction from the heavy phase in the distillation column IV, the low-boiling fraction comprising mainly methanol; and
reusing the methanol in the low-boiling fraction for producing a methyl methacrylate.

2. The process according to claim 1, wherein the heavy phase is separated in the distillation column IV into the low-boiling fraction, a sidestream fraction comprising water and methacrylic acid, and a bottoms fraction comprising water, the strong acid and the at least one alkali metal salt.

3. The process according to claim 1, wherein the stream from the distillation column III comprising methyl methacrylate is admixed with the strong acid and passed into a phase separation, and an organic phase is passed into the extraction and an aqueous phase is passed into the distillation column IV from the phase separation.

4. The process according to claim 1, wherein the stream from distillation column III comprising methyl methacrylate is passed into a mixer into which the strong acid and optionally water are sent, and the strong acid is mixed with the stream comprising methyl methacrylate to obtain a mixture, which is subsequently passed into the phase separator and/or into the extraction.

5. The process according to claim 1, wherein a feeding of the strong acid into the heavy phase from the extraction is effected directly upstream of the distillation column IV.

6. The process according to claim 1, wherein the alkali metal salt is sodium sulfate, the alkali metal methacrylate is sodium methacrylate, and the inorganic acid is sulfuric acid.

7. The process according to claim 1, wherein the light phase from the extraction is fed into at least two further distillation stages and/or a crystallization, and a fraction comprised predominantly of methacrylic acid and a fraction comprised-predominantly of methyl methacrylate are thus obtained.

8. The process according to claim 7, wherein the fraction comprised predominantly of methacrylic acid is esterified with methanol to produce methyl methacrylate.

9. The process according to claim 1, wherein the strong acid is added to a stream downstream of the distillation column III or into the extraction in an amount sufficient to ensure that a pH of the extraction is 3 or more.

10. The process according to claim 1, wherein the low-boiling fractions from the distillation column III and/or the distillation column IV are passed into the reactor II.

11. The process according to claim 2, wherein the low-boiling fraction from the distillation column IV comprises more than 60 wt % of methanol and less than 20 wt % of water, the bottoms fraction comprises more than 60 wt % of water, and the sidestream fraction from the distillation column IV comprises more than 80 wt % of water and less than 5 wt % of methanol.

12. The process according to claim 2, wherein a lower part of the distillation column IV comprises a dividing wall, and wherein column feed is supplied at an upper end of the dividing wall and a draw of the side stream is taken off in liquid form at a different side of the dividing wall where a concentration of the strong acid is less than 0.1 wt % while a content of methanol is less than 1 wt %.

13. The process according to claim 2, wherein a stream from the bottoms fraction from the distillation column IV is sent to a further separating stage to recover water and methacrylic acid and to concentrate the salt-containing waste stream.

* * * * *